(12) United States Patent
Wallace

(10) Patent No.: US 9,259,294 B2
(45) Date of Patent: Feb. 16, 2016

(54) SELF-EVACUATING DENTAL DAM

(75) Inventor: Heath R. Wallace, Weston, OH (US)

(73) Assignee: Heath Wallace, D.D.S.. LLC, Weston, OH (US)

( * ) Notice: Subject to any disclaimer, the term of this patent is extended or adjusted under 35 U.S.C. 154(b) by 379 days.

(21) Appl. No.: 13/040,445

(22) Filed: Mar. 4, 2011

(65) Prior Publication Data

US 2011/0217672 A1  Sep. 8, 2011

Related U.S. Application Data

(60) Provisional application No. 61/310,549, filed on Mar. 4, 2010.

(51) Int. Cl.
*A61C 5/14* (2006.01)
*A61C 5/12* (2006.01)
*A61C 17/06* (2006.01)

(52) U.S. Cl.
CPC ............... *A61C 5/122* (2013.01); *A61C 17/043* (2013.01)

(58) Field of Classification Search
CPC .............................. A61C 17/043; A61C 17/04
USPC ............... 433/136–140, 91–96, 215, 229, 39, 433/155; 600/237–240, 242–243; 128/859–861, 848
See application file for complete search history.

(56) References Cited

U.S. PATENT DOCUMENTS

| | | | | |
|---|---|---|---|---|
| 1,947,389 | A * | 2/1934 | Fried | 433/96 |
| 3,396,468 | A * | 8/1968 | Dayhoff | 433/93 |
| 3,772,790 | A | 11/1973 | Swan-Gett et al. | |
| 4,240,789 | A * | 12/1980 | Rosenthaler | 433/136 |
| 4,261,697 | A * | 4/1981 | Newitter | 433/137 |
| 4,664,628 | A * | 5/1987 | Totaro | 433/136 |
| 4,695,253 | A * | 9/1987 | Tysse | 433/136 |
| 5,931,673 | A | 8/1999 | Bolbolan | |
| 6,152,886 | A * | 11/2000 | Phelan | 600/571 |
| 7,018,206 | B2 * | 3/2006 | Heasley | 433/136 |
| 7,347,691 | B1 * | 3/2008 | Kelly, Sr. | 433/91 |
| 2004/0197732 | A1 * | 10/2004 | Sullman | 433/94 |

* cited by examiner

*Primary Examiner* — Yogesh Patel
(74) *Attorney, Agent, or Firm* — Fraser Clemens Martin & Miller LLC; Michael E. Dockins

(57) ABSTRACT

A fluid evacuating dental dam is disclosed, the fluid evacuating dental dam including a manifold having at least one aperture formed therein, a dental dam selectively attached to the manifold, a suction device in fluid communication with the manifold, and selectively removable cover members disposed over the aperture of the manifold.

20 Claims, 6 Drawing Sheets

SELF-EVACUATING DENTAL DAM

CROSS-REFERENCE TO RELATED APPLICATION

This application claims the benefit of priority of U.S. Provisional Patent Application Ser. No. 61/310,549 filed on Mar. 4, 2010 hereby incorporated herein by reference in its entirety.

FIELD OF THE INVENTION

The invention relates generally to dental appliances, and more particularly to a fluid evacuating dental dam.

BACKGROUND OF THE INVENTION

Dental dams are well known in dentistry for maintaining a dry field for dental work in progress, and to prevent dental debris from entering the mouth and throat of a patient. Conventional rubber dam structures utilize a U-shaped extraoral metal frame to which a piece of rubber sheeting is attached. The rubber sheeting is the dental dam. Prior to being disposed in a mouth, the rubber sheeting is perforated for projection of the tooth (or teeth) therethrough, thereby isolating the tooth/teeth. Clamps are then used to hold the dam around the isolated teeth. Finally, the dentist stretches the periphery of the rubber dam over the extraoral frame, outside the mouth, to keep the dental dam held taut in front of the patient's face. High speed dental drills that use water as a cooling medium for the tooth may cause a considerable water discharge over the face of the dam. The water discharge necessitates the use of a suction tube handled by a dental assistant to maintain a dry field of work and to militate against the water from flowing onto the patient. Some of the water from the drill may flow under the dental dam and into the patient's mouth. Water that flows under the dental dam and saliva that forms thereunder must also be suctioned by the dental assistant to maintain the dry field.

However, existing dental dams have several disadvantages. One disadvantage is that installing such dental dams requires the dentist to take the time-consuming steps described above. When installed, the dental dams are imposing and uncomfortable, and the patients are required to leave their mouths open during the entire dental procedure. Further, the dental dams are flimsy and may collapse. For example, the rubber dental dam my come free from the frame and/or the clamp may come off the tooth. This is especially problematic where patients are young children who are impatient and frightened by the dental dams.

Other dental dams known in the art include a manifold for evacuating fluid from the patient's mouth to maintain a dry field. Such manifolds typically include a plurality of apertures. The apertures are disposed above the dental dam and cannot suction fluids from below the dental dam. The manifold is in communication with a suction device that draws the fluid from the patient's mouth and into the apertures of the manifold. If the suction force provided by the suction device is insufficient, the field may not be sufficiently dried. If the suction force is too great, the dental dam, the patient's cheek, or other materials may occlude the apertures of the manifold. Furthermore, the apertures formed in such manifolds are randomly disposed and may be adjacent teeth that the dentist is not working on.

It would be desirable to develop a fluid evacuating dental dam including a manifold having apertures formed therein, the apertures having cover members for selectively opening the apertures disposed thereon or therein and/or a means for militating against occlusion thereof during use.

SUMMARY OF THE INVENTION

Concordant and congruous with the present invention, a fluid evacuating dental dam including a manifold having apertures formed therein, the apertures including a means for selectively opening the apertures and/or a means for militating against occlusion thereof during use has surprisingly been discovered.

In one embodiment of the invention, a fluid evacuating dental dam comprises a manifold having a substantially u-shape including a pair of substantially linear portions and a curved portion; a dental dam selectively attached to the manifold; and a suction device in fluid communication with the manifold.

In another embodiment, a fluid evacuating dental dam comprises a manifold having at least one aperture formed therein; a dental dam selectively attached to the manifold; a suction device in fluid communication with the manifold; and a selectively removable cover member disposed over the at least one aperture of the manifold.

In another embodiment, a fluid evacuating dental dam comprises a manifold having a substantially u-shape including a pair of substantially linear portions and a curved portion and a plurality of apertures formed therein, wherein at least one of the apertures is formed in one of the substantially linear portions and at least one other of the apertures is formed in the curved portion; a dental dam selectively attached to the manifold; and a suction device in fluid communication with the manifold.

BRIEF DESCRIPTION OF THE DRAWINGS

The above, as well as other advantages of the present invention, will become readily apparent to those skilled in the art from the following detailed description of a preferred embodiment when considered in the light of the accompanying drawings in which.

DETAILED DESCRIPTION OF EXEMPLARY EMBODIMENTS OF THE INVENTION

The following detailed description and appended drawings describe and illustrate various exemplary embodiments of the invention. The description and drawings serve to enable one skilled in the art to make and use the invention, and are not intended to limit the scope of the invention in any manner.

FIGS. 1-5 show the fluid evacuating dental dam 10 according to an embodiment of the invention. The fluid evacuating dental dam 10 includes a dental dam 12 selectively fixed to a manifold 14 which is in fluid communication with a suction device 16.

The dental dam 12 is a substantially fluid impermeable membrane formed from rubber or another polymeric material. The dental dam 12 is similar to those well known in the art. The dental dam 12 may be fixed to the manifold 14 with an adhesive, a clamp, or another fixing means known in the art. The dental dam 12 may be fixed to the entire manifold 14, or a portion of the dental dam 12 may be fixed to the manifold 14, as desired.

Figure 1:
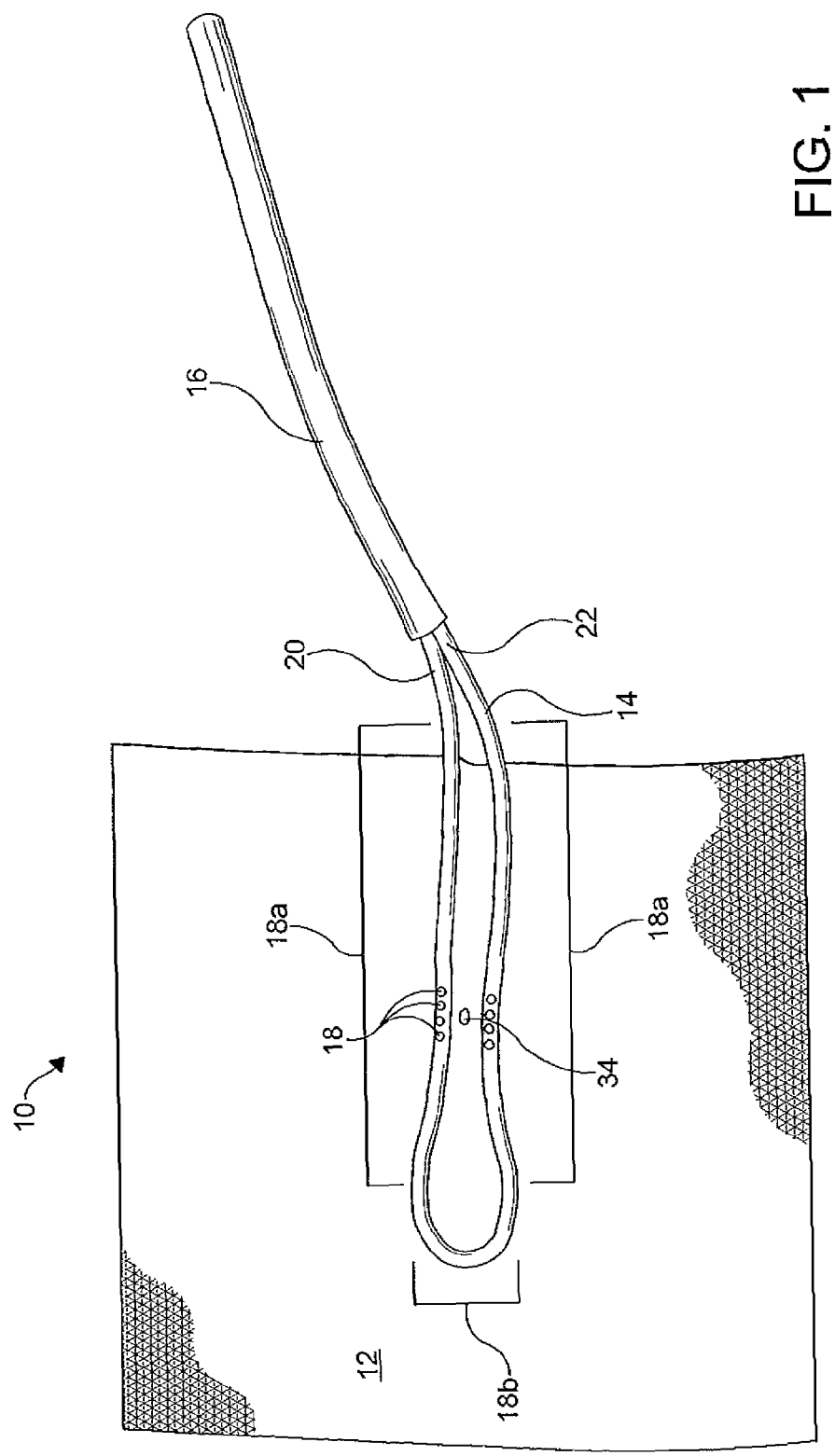
FIG. 1 is bottom plan view of a fluid evacuating dental dam according to an embodiment of the invention.
Figure 2:
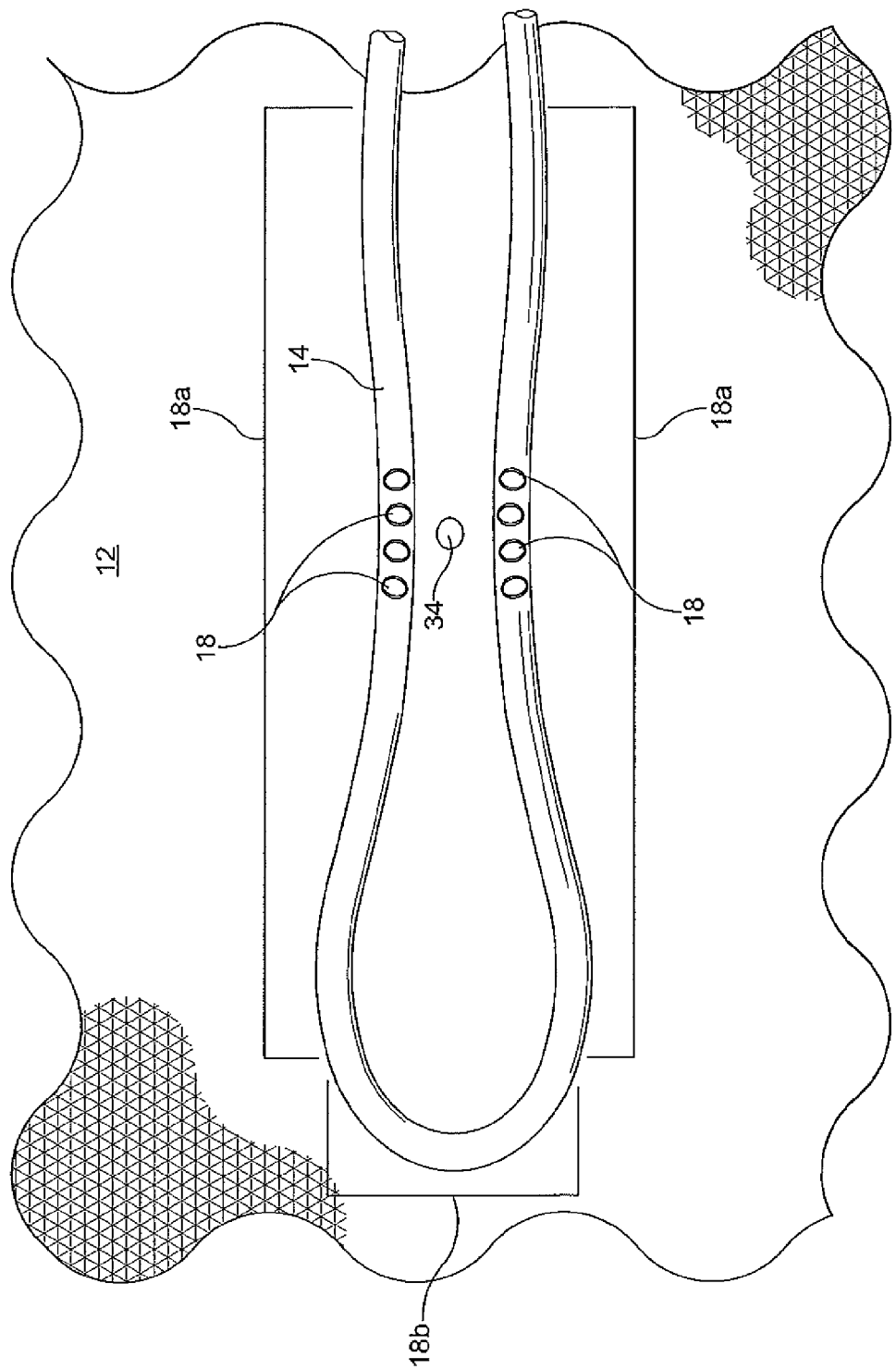
FIG. 2 is an enlarged bottom plan view of the fluid evacuating dental dam of FIG. 1.

The manifold 14 includes a plurality of apertures 18 formed therein in fluid communication with the interior of a patient's mouth. The manifold 14 is substantially circular in cross-section and is formed from a flexible material such as a plastic material, a metallic material, or a composite material, for example. Each of a first end 20 and a second end 22 of the manifold 14 is in fluid communication with the suction device 16. The suction device 16 may be any suction device 16 known in the art. As best shown in FIGS. 1 and 2, the manifold 14 typically forms a U-shaped loop, each side of the loop adapted to be disposed on each side of a tooth/teeth being worked on by a dentist. It has been found that the manifold 14 being disposed on each side of a tooth/teeth provides stability in the dental dam 12 and a tearing thereof is minimized or eliminated. As shown in FIGS. 1-5, each portion of the manifold 12 is disposed on the same side of the dental dam 12.

Figure 3:
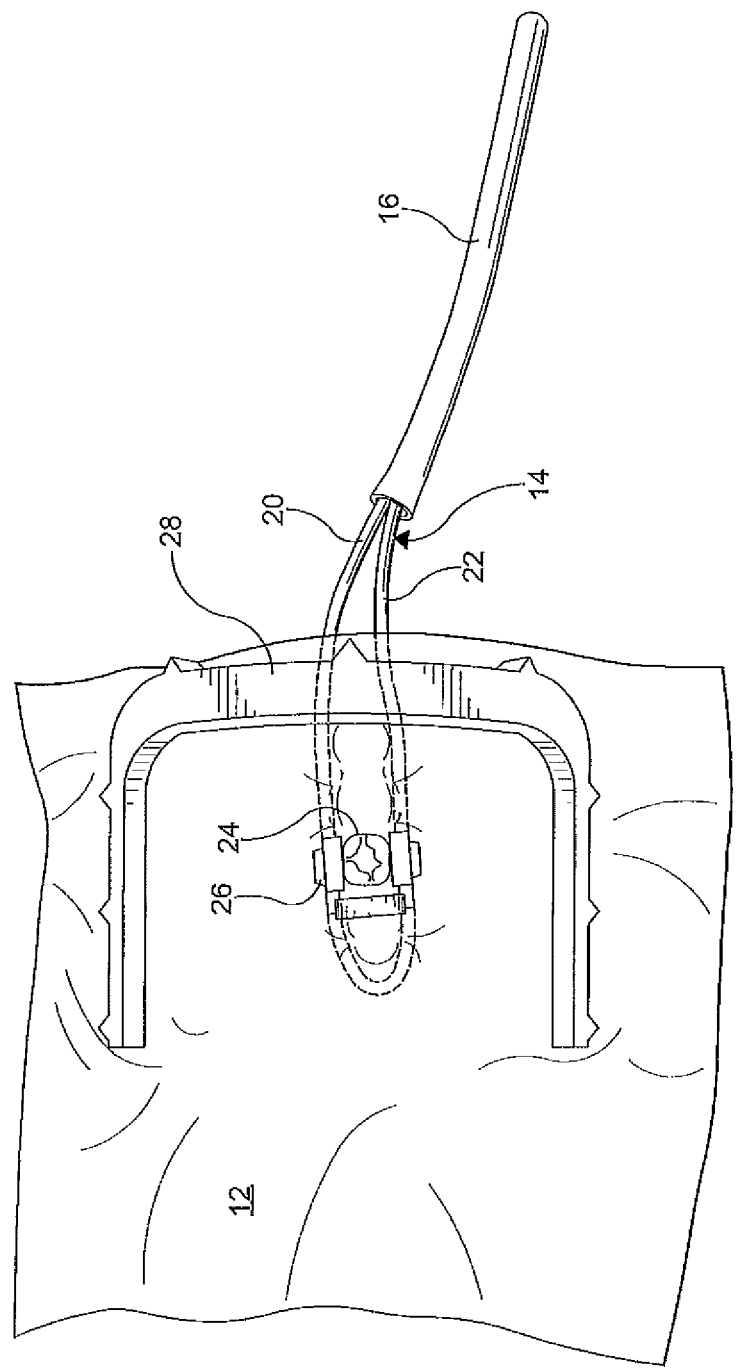
FIG. 3 is a top plan view of a clamped tooth isolated by the fluid evacuating dental dam of FIG. 1.
Figure 4:
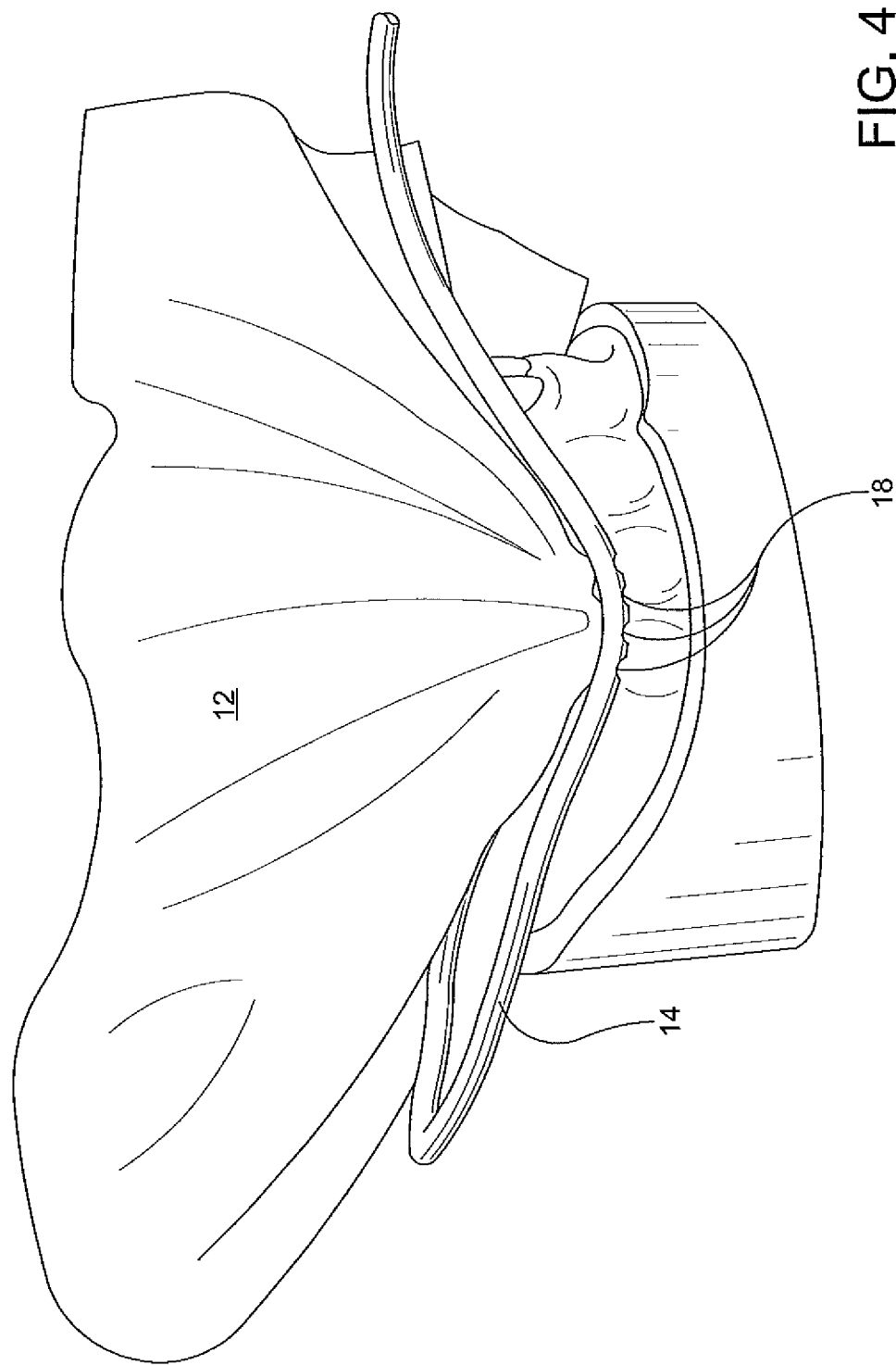
FIG. 4 is a side elevational buccal view of the clamped tooth of FIG. 3 isolated by the fluid evacuating dental dam.
Figure 5:
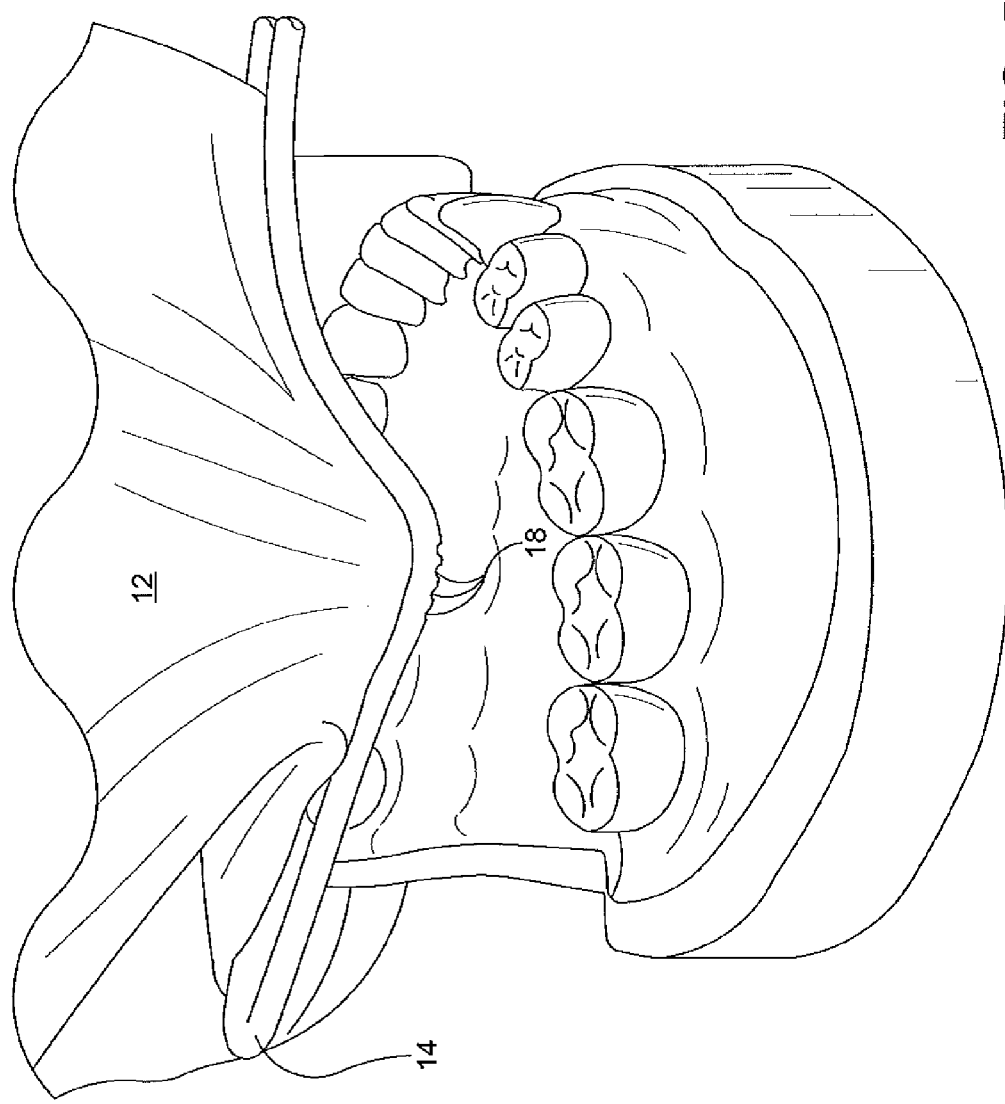
FIG. 5 is a perspective lingual view of the clamped tooth of FIG. 3 isolated by the fluid evacuating dental dam.

The apertures 18 may be formed in substantially linear portions 18a of each side of the loop of the manifold 14 to be disposed on each side of the patient's tooth, or the apertures 18 may be formed in a curved portion 18b of the manifold 14 to be disposed at a back of the patient's mouth posterior of an area to be worked on. Apertures 18 formed in the curved portion 18b of the manifold 14 militate against fluids flowing into the throat of the patient. As shown in FIG. 3, a portion of the dam 12 extends between the linear portions 18a and the curved portion 18b, and another portion extends outward from the linear portions 18a and the curved portion 18b.

Figure 6:
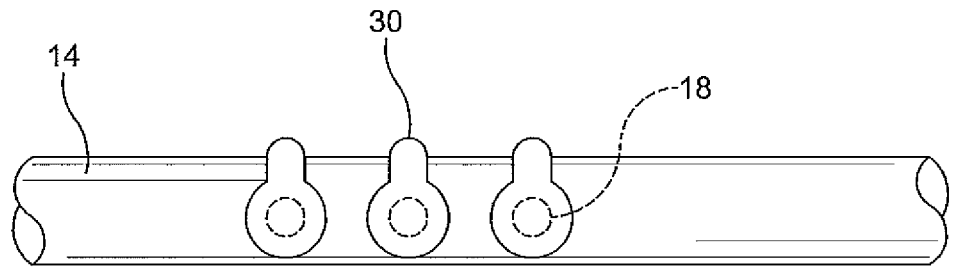
FIG. 6 is a partial top plan view of the manifold of FIG. 1 having selectively removable tabs disposed over apertures formed therein.
Figure 7:
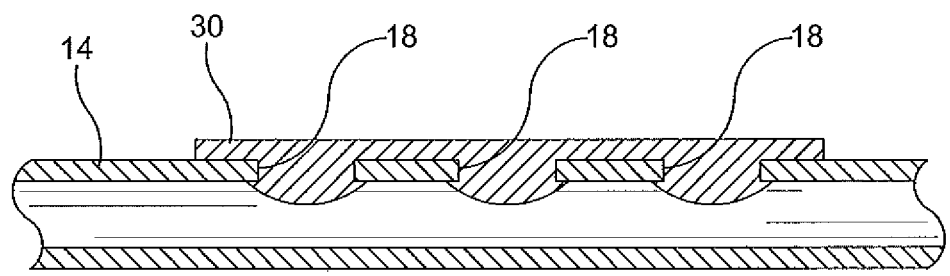
FIG. 7 is a partial cross-sectional view of the manifold of FIG. 1 having selectively removable plugs disposed in apertures formed therein.

Cover members 30 for selectively opening the apertures may be disposed over or in the apertures 18 to militate against introduction of fluid into the apertures 18. The cover members 30 may be a plurality of disposable tabs adhered to the manifold 14 to cover each of the apertures 18, as shown in FIG. 6. Alternatively, the cover members 30 may be strips of material adhered to the manifold 14 to cover a plurality of apertures 18. The cover members 30 may also be replaceable plastic plugs disposed in the apertures 18, as shown in FIG. 7. Each aperture 18 may have an individual plug or a plurality of plugs may be formed on a strip and disposed on a plurality of apertures 18. If the plurality of plugs is formed on the strip, the strip may be removed from the manifold 14 to open a desired plurality of apertures 18 adjacent to a tooth or teeth to be worked on by the dentist. Alternatively, the manifold 14 may include indentations or dimples that may be pierced by a drill or other tool of the dentist in the portion(s) of the manifold 14 to be disposed adjacent a tooth/teeth.

Figure 8:
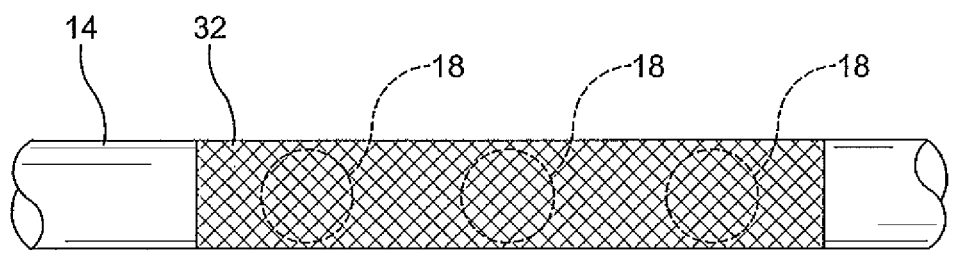
FIG. 8 is a partial top plan view of the manifold of FIG. 1 having a fluid permeable sheath slidably disposed over apertures formed therein.

As shown in FIG. 8, the cover member 30 is a fluid permeable sheath 32 slidably disposed over the apertures 18 of the manifold 14. The permeable sheath 32 may be formed from a foam material or any suitable fluid permeable material. The permeable sheath 32 is adapted to facilitate the flow of fluid from a patient's mouth into the manifold 14 while militating against the suctioning of the dental dam 12, the patient's cheek, or other materials that may occlude the apertures 18 of the manifold 14. It is understood that the cover member 30 may include both a tab(s) or plug(s) and the permeable sheath 32, as desired.

In use, the dental dam 12 of the fluid evacuating dental dam 10 is perforated with an aperture 34 through which a desired tooth/teeth 24 to be worked on may be disposed. The manifold 14 is disposed around the tooth/teeth 24 of a patient with each side of the substantially linear portions 18a of the loop of the manifold 14 disposed on each side of the tooth/teeth 24 of a patient. Prior to positioning the manifold 14 in the patient's mouth, desired cover members 30 are removed from the manifold 14 to provide apertures 18 adjacent to the desired tooth/teeth 24, thereby localizing the suction provided by the suction device 16 to an area adjacent the tooth/teeth 24. The desired tooth/teeth 24 to be worked on are then disposed through the aperture 34 in the dental dam 12, thereby isolating the tooth/teeth 24, as shown in FIG. 3. A clamp 26 is then used to hold the dam 12 around the isolated tooth 24. The dental dam 12 is stretched over a frame 28 to hold the portion of the dental dam 12 extending from the linear portions 18a and the curved portion 18b of the dental dam 12 taut. As a dental drill that uses water as a cooling medium is used on the desired tooth or teeth 24, water discharged therefrom that flows beneath the dental dam 12 near the patient's gums and cheek is removed through the manifold 14. Saliva that forms under the dental dam 12 is also suctioned out of the mouth of the patent through the manifold 14 and away from the tooth/teeth 24 being worked on by the suctioning device 16 without the dentist or dental assistant having to move or lift the dental dam 12. The permeable sheath 32 may be disposed on the manifold 14 to militate against the suctioning of the dental dam 12, a cheek of the patient, or other materials into the apertures 18 of the fluid evacuating dental dam 10.

Figure 9:
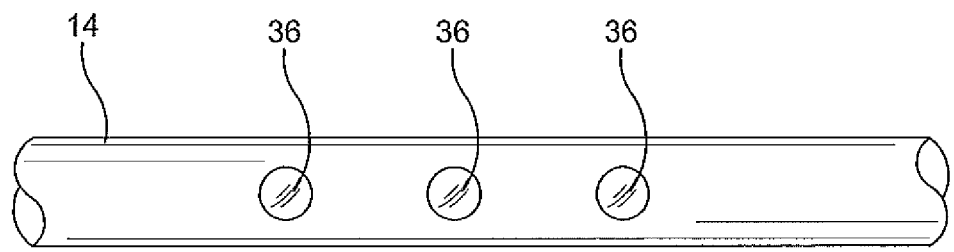
FIG. 9 is a partial top plan view of a manifold having a plurality of dimples formed therein according to another embodiment of the invention.

In another embodiment of the invention, the fluid evacuating dental dam 10 does not include pre-formed apertures 18. The apertures 18 are formed in the manifold 14 by a dentist using a drill and drill bit designed to provide a desired size of aperture 18. The drill and/or bit may include a guard to militate against the drill bit penetrating through two walls of the manifold 14. As shown in FIG. 9, the manifold 14 may also include a plurality of dimples 36 or other indicia formed therein to indicate where a drill bit may be disposed when forming the apertures 18. It is understood that the manifold 14 may include only a single indicia, as desired. It is further understood that the indicia, such as the dimples 36, may be formed from a material with a thinner cross section than a material forming the manifold 14. By having a thinner cross section, the indicia may be more easily penetrated by the drill bit.

From the foregoing description, one ordinarily skilled in the art can easily ascertain the essential characteristics of this invention and, without departing from the spirit and scope thereof, can make various changes and modifications to the invention to adapt it to various usages and conditions.

I claim:

1. A fluid evacuating dental dam for working on teeth comprising:
a manifold having a first end and a second end, and a pair of substantially linear portions and at least one aperture formed in one of the linear portions, each of the pair of linear portions configured to be disposed immediately adjacent to an area to be worked on with the at least one aperture disposed adjacent to the area and the curved portion configured to be disposed posterior of an area to be worked on;

a dental dam adhered to each of the substantially linear portions of the manifold with an adhesive thereby providing stability in the dental dam to minimize a tearing thereof, the manifold adhered to and disposed on an underside of the dental dam, wherein the dental dam is adapted to be selectively perforated to provide an aperture to isolate the area to be worked on from the manifold and areas not to be worked on;

a suction device in fluid communication with each end of the manifold; and a frame configured to cooperate with the dental dam to hold the dental dam taut, wherein the dental dam is disposed between the frame and the manifold.

2. The fluid evacuating dental dam of claim 1, further comprising a removable cover member disposed over the at least one aperture of the manifold, wherein the cover member is a selectively removable tab adhered to the manifold.

3. The fluid evacuating dental dam of claim 1, further comprising a removable cover member disposed over the at least one aperture of the manifold, wherein the cover member is a selectively removable plug disposed in the at least one aperture.

4. The fluid evacuating dental dam of claim 1, further comprising a removable cover member disposed over the at least one aperture of the manifold, wherein the cover member is a fluid permeable sheath slidably disposed over the at least one aperture.

5. The fluid evacuating dental dam of claim 4, wherein the cover member is formed from a foam material.

6. The fluid evacuating dental dam of claim 1, wherein the manifold has a substantially u-shape including a pair of substantially linear portions connected by a curved portion.

7. The fluid evacuating dental dam of claim 1, wherein the linear portions of the manifold are disposed on the same side of the dental dam.

8. The fluid evacuating dental dam of claim 1, wherein another aperture is formed in the curved portion.

9. The fluid evacuating dental dam of claim 1, wherein the manifold includes at least one indicia of where an aperture may be formed.

10. The fluid evacuating dental dam of claim 9, wherein the at least one indicia is a dimple.

11. The fluid evacuating dental dam of claim 1, wherein the frame is formed separately from the manifold.

12. A fluid evacuating dental dam for working on teeth comprising:

a manifold having a substantially u-shape including a pair of substantially linear portions connected by a curved portion and a plurality of apertures formed therein, each of the pair of linear portions configured to be disposed immediately adjacent to an area to be worked on and the curved portion configured to be disposed posterior of an area to be worked on, wherein least one of the apertures is formed in one of the substantially linear portions and at least one other of the apertures is formed in the curved portion;

a dental dam adhered to each of the substantially linear portions of the manifold with an adhesive thereby providing stability in the dental dam to minimize a tearing thereof, the linear portions of the manifold disposed on the same side of the dental dam, and wherein the dental dam is adapted to be selectively perforated to provide an aperture to isolate the area to be worked on from the manifold and areas not to be worked on; and a frame configured to cooperate with the dental dam to hold the dental dam taut, wherein the dental dam is disposed between the frame and the manifold.

13. The fluid evacuating dental dam of claim 12, wherein the frame is formed separately from the manifold.

14. The fluid evacuating dental dam of claim 12, further comprising a removable cover member disposed over the at least one aperture of the manifold, wherein the cover member is a selectively removable tab adhered to the manifold.

15. The fluid evacuating dental dam of claim 12, further comprising a removable cover member disposed over the at least one aperture of the manifold, wherein the cover member is a selectively removable plug disposed in the at least one aperture.

16. The fluid evacuating dental dam of claim 12, further comprising a removable cover member disposed over the at least one aperture of the manifold, wherein the cover member is a fluid permeable sheath slidably disposed over the at least one aperture.

17. The fluid evacuating dental dam of claim 16, wherein the cover member is formed from a foam material.

18. The fluid evacuating dental dam of claim 12, wherein another aperture is formed in the curved portion.

19. The fluid evacuating dental dam of claim 12, wherein the manifold includes at least one indicia of where an aperture may be formed.

20. The fluid evacuating dental dam of claim 19, wherein the at least one indicia is a dimple.

* * * * *